United States Patent [19]

Turley et al.

[11] 3,992,488
[45] Nov. 16, 1976

[54] 1-PHOSPHOROSEMICARBAZIDES
[75] Inventors: Richard J. Turley; Richard L. Doerr, both of Orange, Conn.
[73] Assignee: Olin Corporation, New Haven, Conn.
[22] Filed: July 25, 1975
[21] Appl. No.: 599,056

[52] U.S. Cl. .................. 260/923; 8/116 P
[51] Int. Cl.² .......................... C07F 9/02
[58] Field of Search .................. 260/923

[56] References Cited
UNITED STATES PATENTS
2,906,770  9/1959  Debo .................. 260/923 X
2,965,668  12/1960  Tolkmith .................. 260/923

Primary Examiner—Anton H. Sutto
Attorney, Agent, or Firm—F. A. Iskander; T. P. O'Day

[57] ABSTRACT

1-Phosphorosemicarbazides having the formula

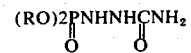

are effective and durable additives for reducing the combustibility of cotton fabrics to which they are applied.

5 Claims, No Drawings

1-PHOSPHOROSEMICARBAZIDES

BACKGROUND OF THE INVENTION

The present invention relates to additives for retarding the flammability of cotton fabrics and to a method for retarding flammability of cotton textiles treated therewith. More particularly, the invention is directed to a novel group of compounds characterized as 1-phosphorosemicarbazides or more specifically as 1-(dialkyl or dihaloalkylphosphoro) semicarbazides.

Recent legislation governing the flammability of certain items of clothing, particularly children's clothing made of cotton has created a need for more effective and durable additives to reduce flammability of cotton fabrics. In particular, there is a need for an additive which will endure at least 50 launderings.

SUMMARY OF THE INVENTION

We have found that certain novel phosphorosemicarbazide additives having the formula

including the lower alkyl and haloalkyl derivatives thereof, when applied to cotton textiles are effective in reducing the combustibility of cotton and will endure the 50 launderings when tested by AATCC Test Method 124—1969.

DETAILED DESCRIPTION

The additives of this invention are 1-phosphorosemicarbazides having the general formula

wherein each R is alkyl having 1–4 carbons, preferably 1–2 carbons or where each R is haloalkyl having 1–4 carbons, preferably 1–2 carbons and wherein the halogen is preferably selected from the group consisting of chlorine or bromine.

The novel compounds are thus phosphorosemicarbazides selected from the group consisting of 1-(dialkylphosphoro) semicarbazides wherein the alkyl component has 1–4 carbons, preferably 1–2 and 1-(dihaloalkylphosphoro) semicarbazides wherein the alkyl component has 1–4 carbons, preferably 1–2 and the halogen component is preferably selected from the group consisting of bromine and chlorine. The compounds specifically preferred are 1-(diethylphosphoro) semicarbazide and 1-[Bis(2-chloroethyl) phosphoro] semicarbazide.

The compounds of the present invention are prepared by reacting a corresponding phosphorochloridate (I) with semicarbazide (II) in accordance with the equation

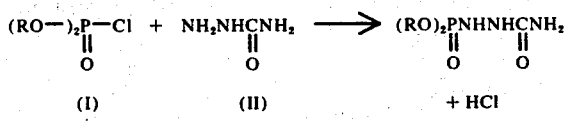

wherein R is as described above. The reaction is suitably conducted at room temperature advantageously 10°–40° C., preferably 20°–30° C., by slowly adding 0.5–2 moles per mole of semicarbazide of the phosphorochloridate to an aqueous solution of semicarbazide with stirring. The HCl formed is neutralized during or after the reaction, the solids collected and dried. To improve purity, the solids may be recrystallized from water or from a mixture of alkanols as shown in the accompanying examples. The N-methylol derivative is then formed by adding the phosphorosemicarbazide to a formaldehyde solution. Suitably, 1–4 moles of formaldehyde, preferably 2–3, on a 100% basis, is employed per mole of phosphorosemicarbazide. The reaction mixture is first adjusted to an alkaline pH, suitably 7–11, preferably 8–10 by the addition of a suitable base such as sodium hydroxide. The reaction suitably proceeds at 50°–100° C. Following completion of the reaction, the reaction mixture is acidified suitably with a mineral acid such as $HNO_3$ or HCl to a pH in the range of 3–6, preferably 4–5 and the remaining components of the final formulation added with stirring.

The remaining components of the formulation include a trimethylolmelamine which acts as a bridge to bond the phosphorosemicarbazide to the fabric. Any trimethylolmalamine may be utilized, for example, the triazineformaldehyde condensate sold by American Cyanamid as *Aerotex* Resin 23 Special. The trimethylolmelamine is suitably employed at a concentration of from about 5–20% based on the total weight of the formulation. The remaining ingredients of the formulaton include a zinc salt such as zinc nitrate hexahydrate $(Zn(NO_3)_2 \cdot 6H_2O)$ to catalyze addition to the fabric.

Thus, the final formulation comprises about 20–40% by weight phosphorosemicarbazide 10–30% by weight formaldehyde (37% basis), at least part of which is believed to be combined as the N-methylol derivative of the phosphorosemicarbazide, from 5–20% by weight of trimethylolmelamine 0.5–2% addition catalyst, balance water.

The resulting formulation was applied to cotton as described in the accompanying examples and then tested for flame retardant properties in accordance with the Standard for the Flammability of Children's Sleepware, DOC FF 3-71 (as amended).

EXAMPLE I

Preparation of 1(Diethylphosphoro-) semicarbazide

A total of 90 g (0.52 moles) diethyl phosphorochloridate was added dropwise in 15 ml increments (80 ml total) to a well-stirred solution of 37.5 g. (0.5 mole) semicarbazide in 160 ml water. After each increment was added, the reaction mixture was stirred for 5 min., followed by addition of a 10 ml portion of NaOH solution (16 g (0.40 mole) NaOH in 40 ml water). Temperature was held at 20°–25° C. throughout the course of the reaction. After the reaction was completed, the solids were collected, washed with water, and thoroughly dried. Yield was 65% of product having a melting point of 192°–193° C. This product was recrystalized from alcohol by first dissolving in hot methanol followed by the addition of a equivalent volume of ethanol. Filtration removed some gummy insolubles. The product obtained from the alcohol solution had a melting point of 197°–200° C. The assigned structure was confirmed by I. R., NMR, and MS.

Calcd. for $C_5H_{14}N_3O_4P$: %C, 28.44; %H, 6.64; %N, 19.90; %P, 14.69.

Found: %C, 28.64; %H, 6.71; %N, 20.14; %P, 14.49.

EXAMPLE II

Preparation of 1-[Bis(2-chloroethyl) phosphoro-] semicarbazide

A total of 183 g (0.75 mole) bis(2-chloroethyl) phosphorochloridate in 40 ml glyme (1,2-dimethoxyethane) was added dropwise at 30°–36° C. to a well-stirred solution of 169 g (2.25 mole) semicarbazide in 470 ml water and 180 ml glyme. The mixture was stirred at about 35° C. for 1.5 hours after addition was completed. The solid precipitate was removed by filtration. After the filtrate was treated with 30 g (0.75 mole) sodium hydroxide in 75 ml water, an additional 180 g (0.75 mole) bis(2-chloroethyl) phosphorochloridate in 40 ml glyme was similarly added to the solution. The mixture was stirred overnight at room temperature, then the precipitate was removed by filtration. The combined solids were crystallized from 500 ml water to give 227 g (54% based on phosphorochloridate) of product, melting point of 168°–174° C. Recrystallization from 1500 ml methanol and 100 ml water yielded 146 g (35% yield) product as well defined plates having a melting point of 183°–185° C. with decomposition.

Calcd. for $C_5H_{12}Cl_2N_3O_4P$: %C, 21.43; %H, 4.29; %Cl, 25.36; %N, 15.00; %P, 11.07.

Found: %C, 21.26; %H, 4.20; %Cl, 25.53; %N, 15.12; %P, 10.89.

EXAMPLE III

Preparation of N-methylol derivative

The N-methylol derivatives of the compounds prepared in Examples I and II were prepared by adding 1 mole of compound to 2 moles of formalin which was adjusted to a pH of 8–10 with caustic soda. The reaction was conducted at 80° C. with gentle stirring for a period of 0.5 hours. Following completion of the reaction, sufficient $HNO_3$ was added to the reaction mixture to adjust the pH thereof to 4.5.

EXAMPLE IV

Formulation and Application

The final formulation was prepared from 142 grams of the product of Example III, containing 80 g of phosphorosemicarbazide 62 g of formalin (37%), 27 g trimethylolmelamine, 4.2 g $Zn(NO_3)_2 \cdot 6H_2O$ and 120 g water. The formulation was applied to cotton print cloth on a three roll padder using one dip and 2 nips. Roll pressure was adjusted to give 70–80% wet pick up of solution. The impregnated samples were placed on pin frames under moderate tension and dried at 200° F. for 1.5 minutes, followed by curing at 340° F. for five minutes in a forced draft oven.

The cured fabrics were tested for flammability before and after machine washing utilizing the Standard for the Flammability of Children's Sleepwear, DOC FF 3-71 (as amended). Durability of the additive finish was tested by normal home launderings procedures (AATCC Test Method 124-1969) in hot water utilizing a phosphate detergent (AATCC No. 124). The cloth was dried between washings in a tumble drier.

The results are reported in Tables I and II for 1-(diethylphosphoro-) semicarbazide and 1-[Bis-(2-chloroethyl) phosphoro] semicarbazide respectively. The ethyl ester (Table I) was shown to be durable to 50 launderings when used with trimethylolmelamine. Elemental analysis of the treated cloth showed 71% of the phosphorus originally present was retained after 50 washes. Leachable phosphorus was removed within the first five washes. From the fifth wash little change in phosphorus content occurred.

1-[Bis-(2-chloroethyl) phosphoro] semicarbazide cured at 340° F. for 5 minutes produced a slight discoloration of the cotton fabric. It was found that this discoloration was readily controlled by utilizing lower cure temperature. In view of the limited loss of leachable phosphorus after 5 washings the tests for this compound were limited to 5 washings comparing various cure temperatures. A cure temperature as low as 220° F. could be utilized and still impart adequate flame retardancy and durability to the fabric.

Table I

| Washes | Flamability* Rating | %P |
|---|---|---|
| 0 | SE 2.5" | 3.28 |
| 1 | SE 3.5" | 2.58 |
| 5 | SE 3.5" | 2.37 |
| 10 | SE 5.0" | 2.53 |
| 15 | SE 3.3" | 2.45 |
| 20 | SE 3.0" | 2.28 |
| 35 | SE 3.0" | 2.73 |
| 50 | SE 3.3" | 2.32 |

Table II

| Cure Temp./ Time ° F/5 min. | Flammability Rating* Before Washing | After 5 Washes |
|---|---|---|
| 200 | B | B |
| 220 | SE 2.5" | SE 2.5" |
| 240 | SE 2.5" | SE 2.0" |
| 250 | SE 3.0" | SE 2.5" |
| 280 | SE 2.0" | SE 2.0" |
| 300 | SE 2.5" | SE 3.0" |

*B indicates sample burned entire length. SE indicates fabric self extinguished with char length expressed in inches.

What is claimed is:

1. A composition of matter comprising a phosphorosemicarbazide having the formula:

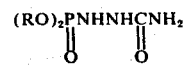

wherein each R is selected from the group consisting of alkyl having 1–4 carbons and haloalkyl having 1–4 carbons wherein the halogen component is selected from the group consisting of bromine and chlorine.

2. The composition of claim 1 wherein each R is alkyl having 1–4 carbon atoms.

3. The composition of claim 1 wherein each R is ethyl.

4. The compositon of claim 1 wherein each R is haloalkyl having 1–4 carbon atoms.

5. The composition of claim 4 wherein each R is chloroethyl.